United States Patent
Stack

[19]

[11] Patent Number: 5,342,393
[45] Date of Patent: Aug. 30, 1994

[54] METHOD AND DEVICE FOR VASCULAR REPAIR

[75] Inventor: Richard S. Stack, Durham, N.C.

[73] Assignee: Duke University, Durham, N.C.

[21] Appl. No.: 935,900

[22] Filed: Aug. 27, 1992

[51] Int. Cl.⁵ .............................................. A61B 17/00
[52] U.S. Cl. ..................... 606/213; 606/215; 604/15; 24/453; 411/339; 411/510; 411/908
[58] Field of Search ................. 606/213–215, 606/220, 232, 139; 604/15, 60, 158, 159, 167, 218, 288; 24/453, 107, 108, 662; 411/338, 339, 508–510, 913, 908

[56] References Cited

U.S. PATENT DOCUMENTS

| | | | |
|---|---|---|---|
| 3,874,388 | 4/1975 | King et al. | 606/213 |
| 4,007,743 | 2/1977 | Blake | 606/232 |
| 4,532,926 | 8/1985 | O'Holla | 606/220 |
| 4,719,917 | 1/1988 | Barrows et al. | 606/220 |
| 4,744,364 | 5/1988 | Kensey | 606/213 |
| 4,759,670 | 7/1988 | Linder et al. | 411/339 |
| 4,852,568 | 8/1989 | Kensey | 606/213 |
| 4,890,612 | 1/1990 | Kensey | 606/213 |
| 5,021,059 | 6/1991 | Kensey | 606/213 |
| 5,061,274 | 10/1991 | Kensey | 606/213 |
| 5,171,259 | 12/1992 | Inoue | 606/232 |

FOREIGN PATENT DOCUMENTS

WO9205740 4/1992 PCT Int'l Appl. .

*Primary Examiner*—Stephen C. Pellegrino
*Assistant Examiner*—Gary Jackson
*Attorney, Agent, or Firm*—Cushman, Darby & Cushman

[57] ABSTRACT

A method and device are provided for sealing a perforation in the wall of, for example, a blood vessel. The device is in the form of a two part closure which seals the hole by clamping the tissue surrounding the hole from both the inside and the outside of the vessel. In accordance with one exemplary embodiment, two rivet portions are provided which are bayonet or screw threadedly interlocked to clamp the vessel wall about the perforation. An alternate embodiment applies heat to couple the rivet parts as well as to cauterize the wound site. Heat may also advantageously be used to separate the rivet from its delivery system.

22 Claims, 5 Drawing Sheets

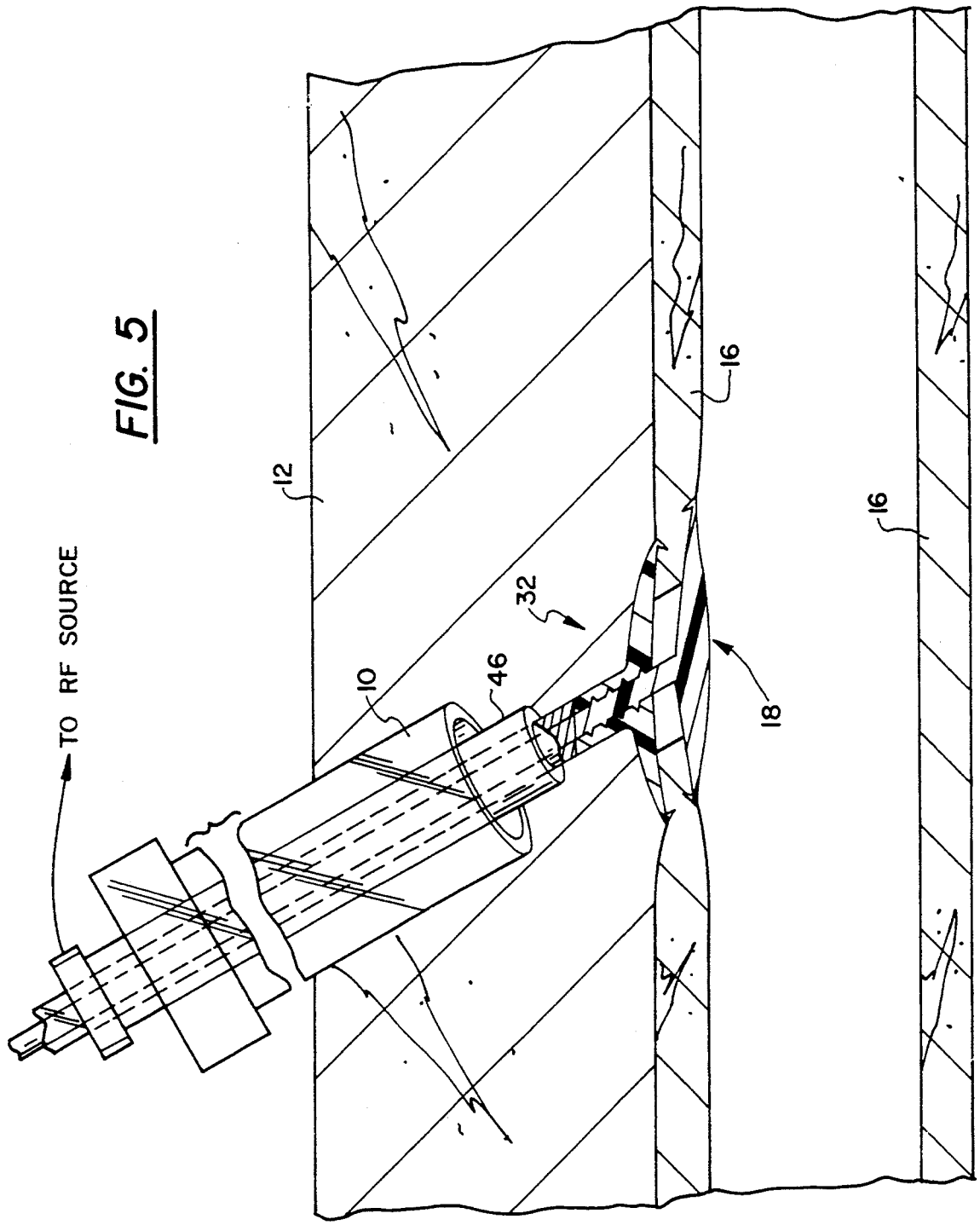

METHOD AND DEVICE FOR VASCULAR REPAIR

BACKGROUND OF THE INVENTION

1. Field of the Invention

The present invention relates to methods and devices for repairing perforations and/or incisions in the wall of a hollow organ or body passage and, in particular, to a rivet-like device for sealing an opening in a blood vessel.

2. Description of the Related Art

A variety of surgical procedures which have now become common place are carried out intraluminally. Thus, a body duct such as a blood vessel is pierced and a catheter is inserted therethrough so that instruments can be inserted into the duct and/or the physician can inject radiographic contrast medium to view the physiology of the duct. Such procedures necessarily leave an aperture in the wall of the duct which must be sealed upon completion of the procedure. Punctures in blood vessels are of particular concern because of the problem of bleeding at the puncture site.

In the past, bleeding has been stopped by the application of pressure over the puncture site sufficiently long for hemostasis to occur. Such application of pressure results in a significant reduction if not a complete cessation of blood flow through the vessel in question and does not effectively prevent all hemorrhaging at the puncture site. Furthermore, when the patient has been dosed with anticoagulants, for example, it is particularly difficult to cease bleeding simply by applying manual pressure and it may be necessary to suture the blood vessel.

It has been previously proposed to insert a plug into the blood vessel and apply that plug against the inner surface of the blood vessel to close the puncture in the blood vessel wall. See, e.g., Kensey U.S. Pat. Nos. 4,744,364, 4,852,568, 4,890,612, 5,021,059 and 5,061,274. Typically, the Kensey plugs are held in a vessel sealing position by retracting a cord which extends from the plug and securing it to the patient's skin.

Another approach is typified by the Vasoseal, marketed by DataScope. That concept is basically the opposite of the Kensey-type device. It operates by sealing near the hole in the blood vessel from the outside by injecting liquid collagen in the track of the sheath as it is being withdrawn from the vessel.

Yet another approach is a vessel plug (PCT publication No. WO 92/05740) which like Vasoseal plugs the vessel from the outside only.

The disadvantage of the above described products and processes is that, because they are applied against only one face of the wound, they often do not form an effective enough seal and may be cumbersome to use.

SUMMARY OF THE INVENTION

The present invention provides a method and device for sealing a perforation in the wall of a body duct or hollow body organ such as a blood vessel, in the form of a rivet which closes the hole by stapling or clamping the tissue surrounding the hole from both the inside and the outside of the vessel. In accordance with one exemplary embodiment of the invention inner and outer rivet portions are provided which are bayonet or screw threadedly interlocked to clamp the vessel wall about the perforation. An alternate embodiment applies heat to couple the rivet parts as well as to cauterize the wound site. Heat may also advantageously be used to separate the rivet from its delivery system.

BRIEF DESCRIPTION OF THE DRAWINGS

FIG. 5 is an enlarged, schematic cross-sectional view of an alternate embodiment of the invention.

DETAILED DESCRIPTION OF THE PRESENTLY PREFERRED EXEMPLARY EMBODIMENT

Although the invention is described herein with reference to the closure of a puncture or incision in a blood vessel it should be appreciated that the principles and structure of the invention could be utilized to seal an incision or puncture in a hollow organ or through another body duct such as a fallopian tube, bile duct, or the like.

Figure 1:
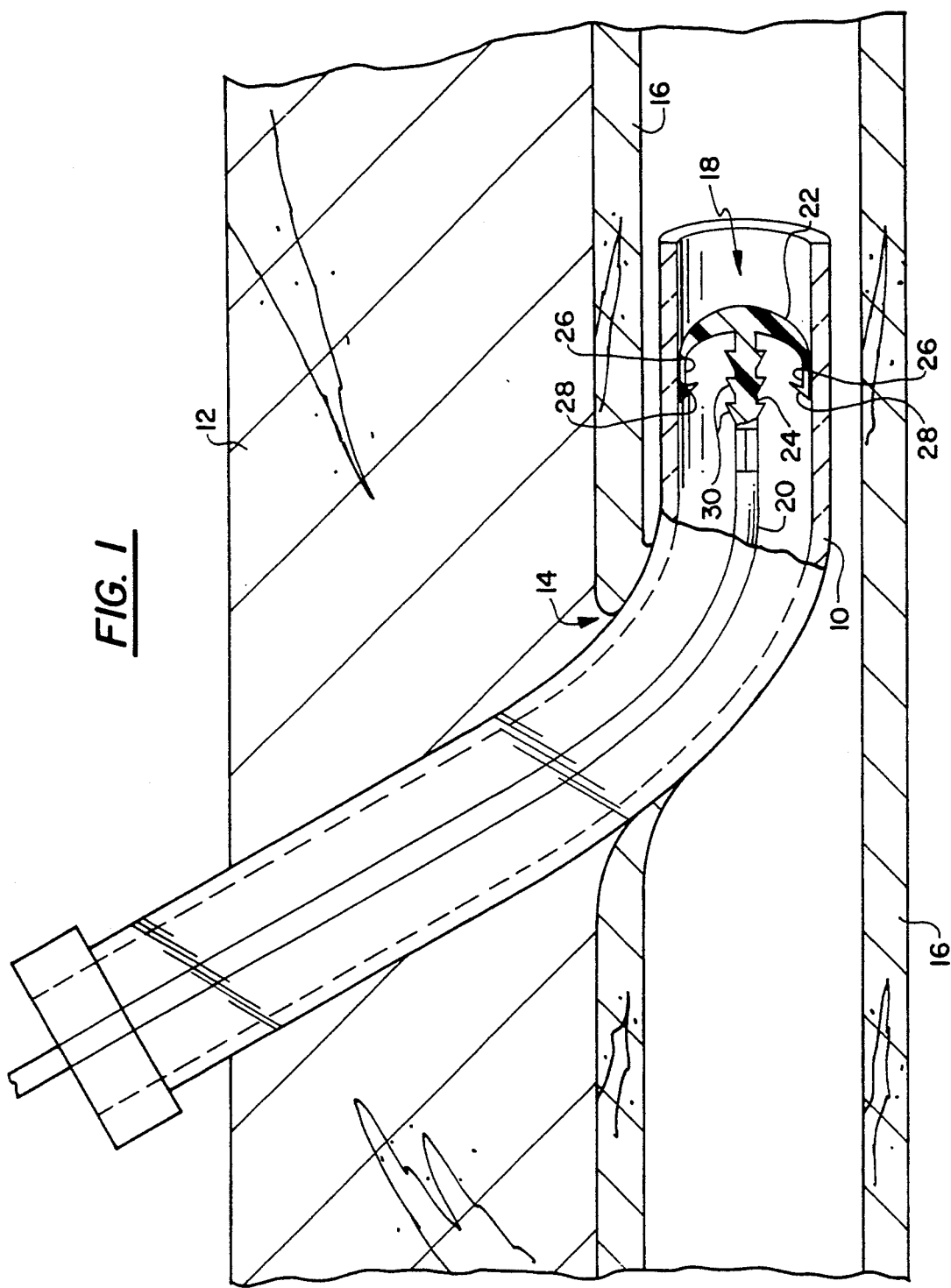
FIG. 1 is an enlarged, schematic cross-sectional view showing the delivery of an inner rivet portion in accordance with the invention.

FIG. 1 illustrates a catheter or guide sheath 10 extending percutaneously or through the skin 12, through a puncture 14 in a blood vessel 16, and into the interior of the blood vessel. In accordance with the invention, once the surgical or diagnostic procedure has been completed, any and all instruments and/or catheters are removed but the guide sheath 10 is maintained in place providing access to the interior of the blood vessel 16. When it is desired to remove that sheath 10 and seal the puncture 14 in the blood vessel 16, an inner rivet portion 18 and insertion tool assembly 20 in accordance with the invention is inserted through the sheath 10.

The inner rivet includes a plate portion 22 and a stem portion 24. The plate portion 22 may include peripheral tabs 26 to facilitate flexure and passage of that plate portion through the delivery sheath 10 as well as to ensure a wide distribution of the gripping force of the rivet. In addition, prongs, tines, or other like means 28 for engaging and griping the tissue may be provided on the plate portion and/or tabs to ensure the patency of the seal.

Furthermore, means 30 are provided on the stem of the inner rivet portion for engaging or coupling the inner rivet to an outer rivet portion 32. As detailed more fully below, the interlocking structure may be interlocking ridges or screw threads, or the two components may be heat sealed together in lieu of or in addition to providing a coupling means on their respective stems.

As illustrated, the plate and tab portion 22 of the inner rivet 18 has a maximum diameter greater than the diameter of the sheath 10, such that it is distorted during the insertion process. The material of the rivet inner portion 18 is selected so that it may be deflected as shown but is resilient and rigid enough to resume substantially its maximum diameter upon full insertion, out of the sheath 10. As noted above, the peripheral portion of the inner rivet may be in the form of a series of tabs 26 provided that the remainder of the rivet has a diameter great enough to define a closure for the puncture 14.

Figure 2:
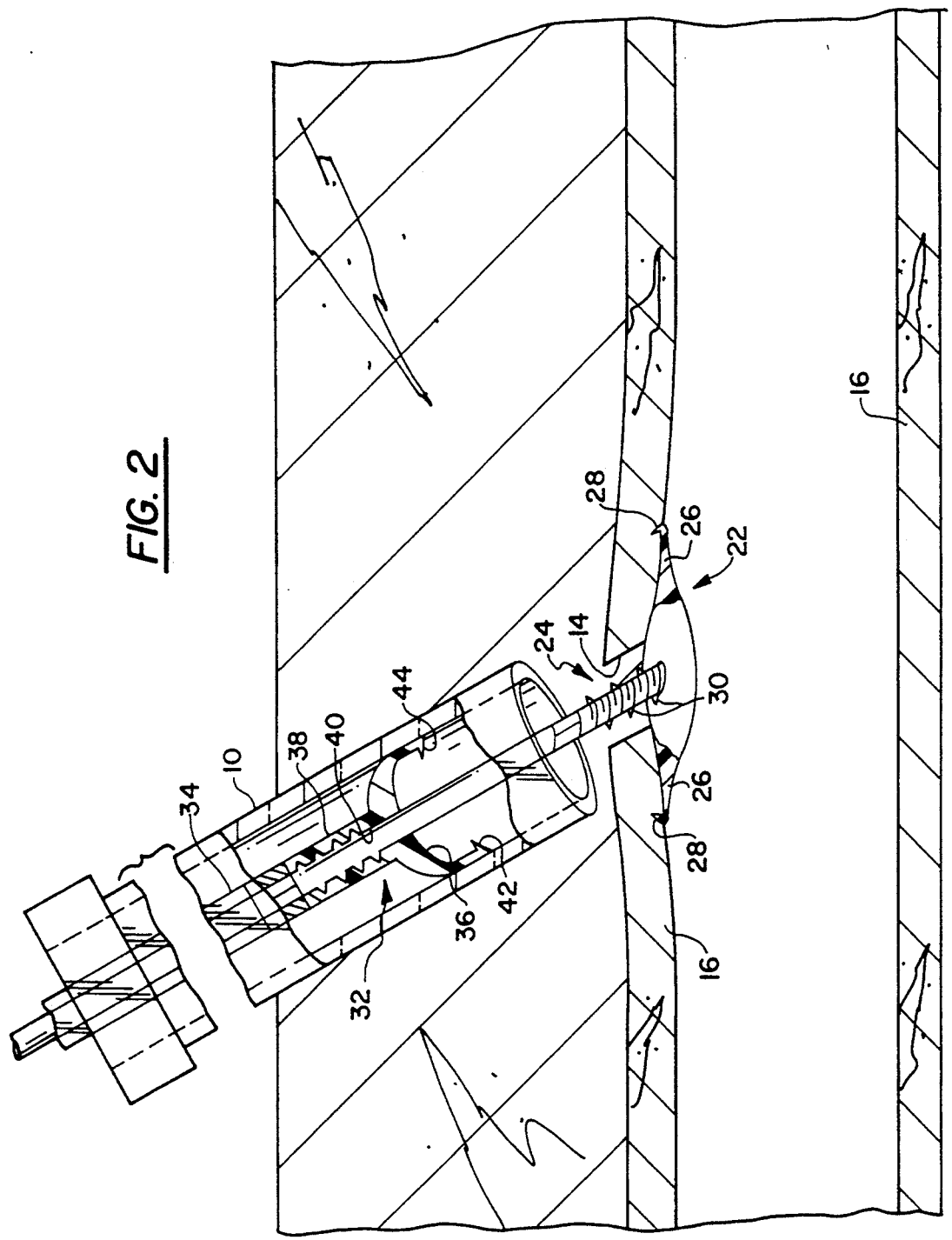
FIG. 2 is an enlarged, schematic cross-sectional view showing delivery of an outer rivet portion in accordance with the invention.

After the inner rivet 18 has passed through the sheath 10 and into the blood vessel 16, the sheath 10 is withdrawn proximally through the outer wall of the blood vessel so that it is disposed within the tissue adjacent the vessel wall. The inner rivet portion can then be brought into engagement with the inner wall of the blood vessel to thereby seal the same at the puncture site (FIG. 2). In addition, the vessel wall tends to retract in towards the stem and stalk once the sheath is removed, facilitating formation of a seal with the inner rivet portion. The rivet insertion tool 20 is held in tension with the inner rivet portion engaging the vessel wall to maintain hemostasis.

An outer rivet portion 32 and insertion tool assembly 34 in accordance with the present invention is then fed concentrically along stalk 20 of the inner rivet insertion tool.

The outer rivet 32 includes a plate portion 36, which may include tabs 44, and a stem portion 38 and is distinguished from the inner rivet portion 18 in that a hole or bore 40 is defined through the stem 38 and plate 36. The bore 40 has an inner diameter substantially corresponding to the outer diameter of the stem 24 of the inner rivet portion 18. Furthermore, tines or prongs 42 may optionally be provided for gripping the tissue surrounding the puncture or aperture 14 through the blood vessel wall 16. When provided, the tines or prongs 42 extend so as to face the outer surface of the wall 16 of the blood vessel. Preferably the tines or prongs 42 are inclined so that they do not resist the coupling action of the outer rivet 32 to the inner rivet 18 but do resist decoupling of the rivets. Thus, if the inner and outer rivets are screw threaded together, the prongs or tines of the outer rivet portion, if provided, are inclined so that they do not oppose threading together but they resist unscrewing.

The insertion stalk 34 of the outer rivet is detachably coupled to the outer rivet portion 32 as is the insertion stalk for the inner rivet portion, the primary distinction between the stalks of one and the other being that the insertion stalk 34 for the outer rivet portion is hollow so that it can be threaded over and along the insertion stalk 20 of the inner rivet portion.

As is apparent, when the inner rivet portion is retracted its stem 20 extends through the hole or puncture 14 in the vessel wall 16 and the plate 22 closes the inner periphery of the perforation 14 with its gripping tines or prongs 28 engaging and gripping the tissue, thereby preventing full retraction of the inner rivet through the aperture in the blood vessel and holding the same in place blocking blood flow out through the vessel wall. The retraction of the vessel wall toward the stem also resists displacement of the inner plate back through the hole or puncture. Although tines may be provided on the outer rivet, as noted above, because it is envisioned that the outer rivet would be moved, shifted or otherwise rotated relative to the inner rivet during the attachment process, tines or prongs may be omitted if necessary or desirable to prevent damage to the blood vessel during such shifting motion.

Figure 3:
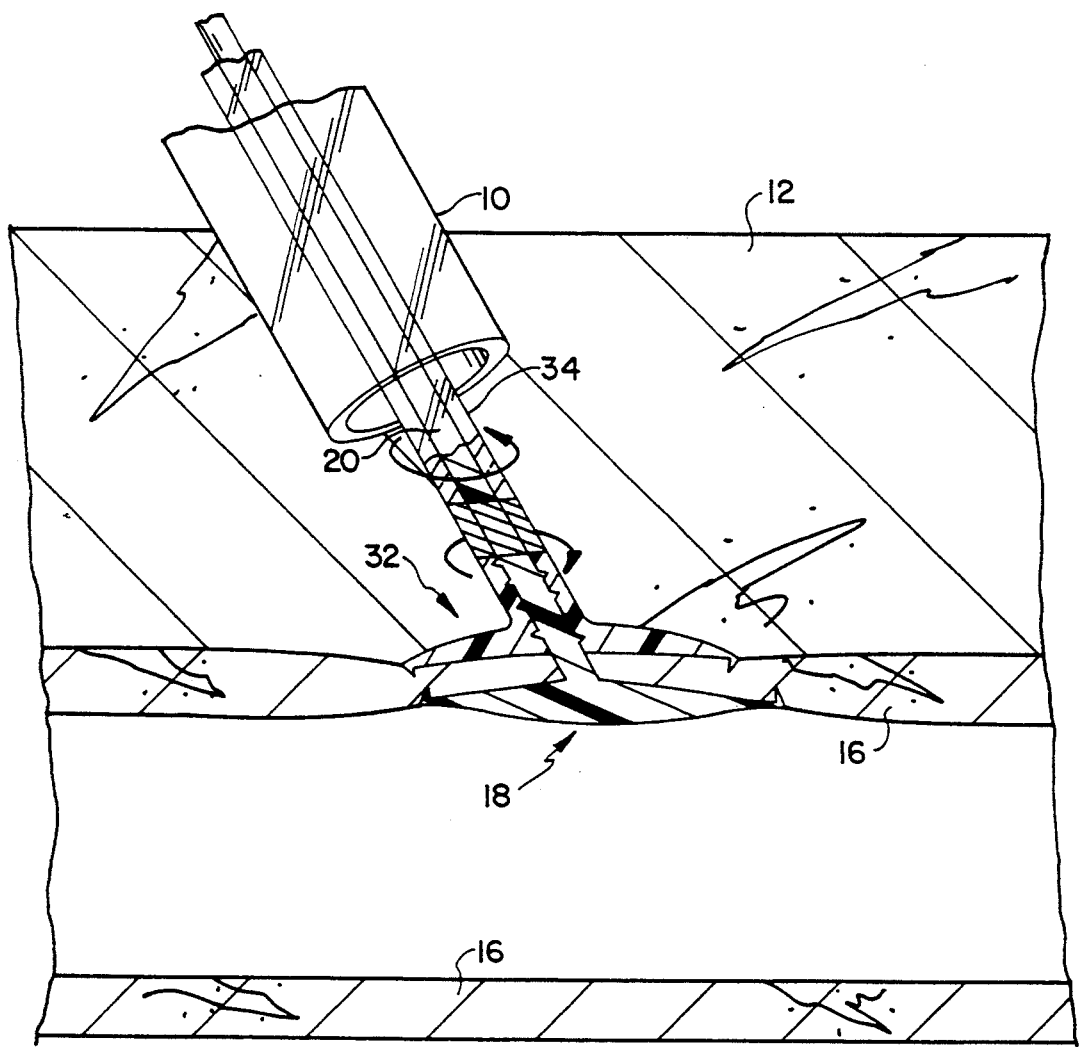
FIG. 3 is an enlarged, schematic cross-sectional view showing attachment of the inner and outer rivet portions in accordance with the invention.
Figure 4:
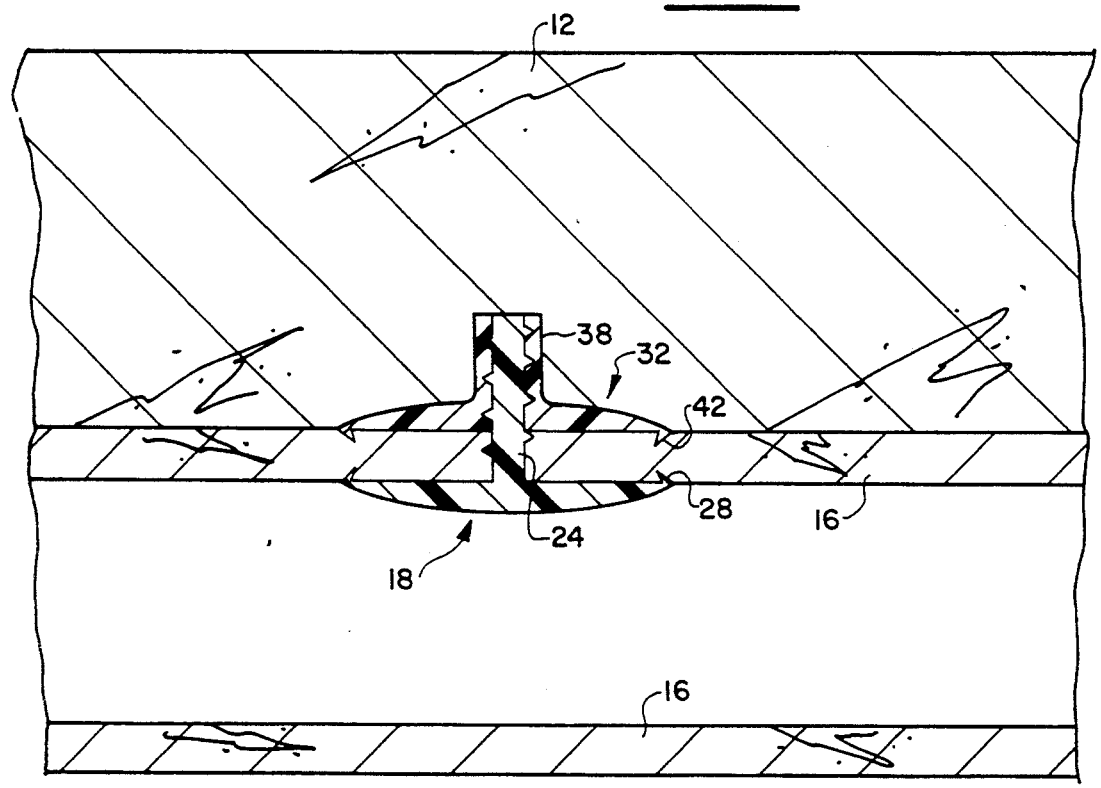
FIG. 4 is an enlarged, schematic cross-sectional view of a secured rivet in accordance with the invention.
Figure 6:
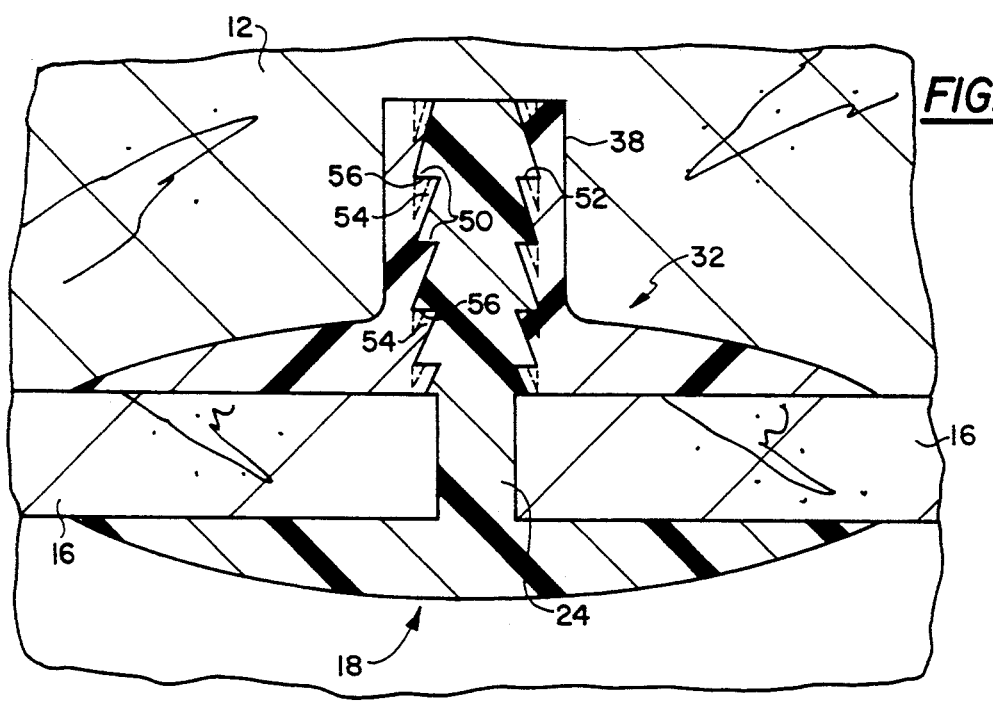
FIG. 6 is an enlarged, schematic cross-sectional view of an alternate embodiment of the secured rivet of the invention.

The outer rivet portion 32, like the inner rivet portion is flexible enough as to be distortable for passage through the sheath but resilient and rigid enough to resume its original configuration in the tissue adjacent the perforated wall of the vessel, upon full insertion through the sheath 10. The outer rivet portion is then fully inserted over the inner rivet portion. The rivet portions are locked together via their interlocking ridges (FIG. 6) or threaded together via screw-like threads (FIGS. 3 and 4).

Thus, the outer surface of the stem of the inner rivet portion may be threaded and the inner surface of the outer rivet portion correspondingly threaded so that opposite rotation of the insertion tools about their longitudinal axes threadably engages the rivets with one another and clamps the tissue surrounding the perforation between the inner and outer rivet portions. In the alternative, the inner rivet stem may have triangular ridges 50 that define horizontal shoulders 52 and the outer rivet may have one or more upside down triangular ridge 54 that defines an opposing shoulder 56 or one or more deflectable tabs (shown in phantom) for engaging an adjacent shoulder 52 to thereby allow the outer rivet to be slid over the inner rivet but prevent separating movement. Thus, as an alternative to screw threads, the locking of the inner and outer portions of the rivet may be by a push pull movement to achieve an interlocking of ridges and/or tabs thereon.

Once the two portions of the rivet are locked together, the stalks can be twisted off in opposite directions or over-torqued in the same direction and removed from the body. More particularly, the stalks may be "bayonet" coupled to the rivet portions, for a twist/pull removal or can be threaded thereto so that continued or reverse twisting motion following attachment of the rivet portions separates the stalks from their respective rivet portions and allows removal of both, either simultaneously or one after the other. As an alternative to a threaded or bayonet type interconnection of the insertion stalks and the respective rivet portions, the separation joint may be formed of a material having a lower melting point of a configuration which can be readily severed through the application of heat. A heat delivering/cauterizer element 46 can then be slidably disposed over the outer rivet portion insertion stalk 34 to direct heat or electrical energy to the separation joint of the stalk 34 and the rivet 32 to thereby allow removal of the stalk from the rivet (FIG. 5). The heat will also cauterize the site to avoid any bleeding. By suitably selecting materials for the rivet portions, furthermore, the application of heat may be used to couple the rivet portions together. The final completed seal with the rivet in place is illustrated in FIG. 4.

The rivet portions may be made from a bio-resorbable polymer, a non-bioresorbable polymer, and/or a biocompatable metal in whole or in part, whether or not partially or wholly porous. Further, each rivet portion can be made from different materials or different combinations of materials. For example, the inner rivet plate and/or stem can be resorbable and the outer rivet plate and/or stem non resorbable or only partially resorbable. The insertion tools or stalks can be metal, non resorbable, or resorbable polymer.

The polymers may be modified to accept drugs. For example, an anticoagulant such as heparin could be applied to the inner rivet to prevent thrombosis on the inner surface of the blood vessel. As another example, a procoagulant (e.g. thrombin) could be incorporated into the inner aspect of the inner plate, both sides of the outer plate and the stems to prevent any bleeding at the puncture site.

What is claimed is:

1. A device for sealing a perforation or incision in a duct or hollow organ comprising:

an inner rivet member including a plate portion having first and second side faces and a stem portion extending from the second side face of said plate portion, said rivet member being made at least in part of a material that is bio-resorbable; and an outer rivet member including a plate portion having first and second side faces and a stem portion extending from said second side face of said plate portion in a direction away from said inner rivet member; said outer rivet member having a central bore extending from said first side face of said plate through the stem portion of said outer rivet member for sleevelike coupling with said inner rivet member stem, said outer rivet member being made at least in part of a material that is bio-resorbable.

2. A device as in claim 1, further comprising means for coupling said inner rivet member to said outer rivet member with said stem portion of said inner rivet member disposed within said bore of said outer rivet member.

3. A device as in claim 1, wherein said stem portion of said outer rivet member has a central bore defined at least partially therethrough for receiving said stem portion of said inner rivet member.

4. A device as in claim 3, further comprising means for coupling said stem portions of said rivet members together.

5. A device as in claim 4, wherein said means for coupling comprise screw threads on said stem portion of said inner rivet member and screw threads defined on walls of said bore of said stem portion of said outer rivet member.

6. A device as in claim 4, wherein said means for coupling comprise at least one ridge element defined on said stem portion of said inner rivet member, said ridge element having an inclined face and a shoulder, and at least one tab element disposed within said central bore of said stem portion of said outer rivet so as to be deflected by said inclined face to allow sliding placement of said outer rivet over said inner rivet and to engage said shoulder to resist removal of the outer rivet.

7. A device as in claim 4, wherein said means for coupling comprise at least one ridge element defined on said stem portion of said inner rivet member, said ridge element having an inclined face and a shoulder, and at least one ridge member having an inclined face and a shoulder, said ridge member being defined on a wall of said central bore of said stem portion of said outer rivet, said ridge member being deflectable upon engagement with said inclined face to allow sliding placement of said outer rivet over said inner rivet, whereas engagement of said shoulder of said ridge member with said shoulder of said ridge element resists removal of the outer rivet.

8. A device as in claim 1, wherein said plate portion of each of said rivet members includes a plurality of radial tab means for facilitating flexure and passage of said plate portion through the delivery sheath and for distributing a gripping force of the rivet members.

9. A device as in claim 1, wherein at least one prong element is defined on said second side face of said inner rivet member.

10. A device as in claim 1, wherein at least one prong element is defined on said first side face of said outer rivet member.

11. A device as in claim 1, further comprising an inner stalk member detachably coupled to said inner rivet member.

12. A device as in claim 11, further comprising an outer stalk member detachably coupled to said outer rivet member, said outer stalk member having a bore defined therethrough for receiving said inner stalk member.

13. A device as in claim 11, wherein said inner stalk member is threaded to said inner rivet member.

14. A device as in claim 11, wherein said inner stalk member is coupled to said inner rivet member with a heat frangible coupling.

15. A method of sealing a perforation or incision in a duct or hollow organ comprising:

providing an inner rivet member including a plate portion having first and second side faces and a stem portion extending from said second side face of said plate portion;

providing an outer rivet member including a plate portion having first and second side faces, a stem portion extending from said second side face of said plate portion in a direction away from said inner rivet members, and a central bore defined at least partially therethrough for receiving said stem portion of said inner rivet member;

inserting said inner rivet member through said perforation or incision into the interior of the duct or hollow organ;

retracting said inner rivet member so that said plate portion thereof is in engagement with a periphery of said perforation or incision and said stem portion thereof projects through the perforation or incision;

delivering said outer rivet member to a position adjacent to but exterior of the duct or hollow organ;

engaging said inner and outer rivet members so that said stem of said inner rivet member extends into said bore of said outer rivet member at least partially through said stem portion thereof breaking the plane of said plate portion of the outer rivet member; and coupling said inner and outer rivet members.

16. A method as in claim 15, wherein said step of coupling comprises threading said rivet members together.

17. A method as in claim 15, wherein said step of coupling comprises axially sliding to lock at least one of the opposing projections.

18. A method as in claim 15, wherein said step of providing an inner rivet member comprises providing an inner rivet member detachably coupled to an inner stalk element and said step of inserting comprises manipulating said inner stalk element to insert said inner rivet member through a guide catheter into the duct or hollow organ, and further comprising, after said step of coupling, detaching said inner stalk element from said inner rivet member.

19. A method as in claim 18, wherein said step of providing an outer rivet member comprises providing an outer rivet member detachably coupled to an outer stalk element and said step of delivering comprises feeding said outer stalk element over said inner stalk, and further comprising, after said of coupling, detaching said outer stalk element from said outer rivet member.

20. A method as in claim 18, wherein said inner stalk element is coupled to said inner rivet member with a heat frangible coupling and wherein said step of detaching said inner stalk element comprises applying heat to said heat frangible coupling to sever the same.

21. A method as in claim 18, wherein said inner stalk element is threaded to said inner rivet member.

22. A device for sealing a perforation or incision in a duct or hollow organ comprising:

an inner rivet member including a plate portion having first and second side faces and a stem portion extending from the second side face of said plate portion, said rivet member being made at least in part of a porous material to facilitate tissue ingrowth; and an outer rivet member including a plate portion having first and second side faces and a stem portion extending from said second side face of said plate portion in a direction away from said inner rivet member; said outer rivet member having a central bore extending from said first side face of said plate through the stem portion of said outer rivet member for sleeve-like coupling with said inner rivet member stem, said outer rivet member being made at least in part of a porous material to facilitate tissue ingrowth.

* * * * *